(12) United States Patent
Chen et al.

(10) Patent No.: US 9,696,255 B2
(45) Date of Patent: Jul. 4, 2017

(54) IMAGE PROCESSING METHOD OF TWO-PHOTON STRUCTURED ILLUMINATION POINT SCANNING MICROSCOPY

(71) Applicant: National Central University, Taoyuan (TW)

(72) Inventors: Szu-Yu Chen, Taoyuan (TW); Chia-Hua Yeh, Taoyuan (TW)

(73) Assignee: National Central University, Taoyuan (TW)

( * ) Notice: Subject to any disclaimer, the term of this patent is extended or adjusted under 35 U.S.C. 154(b) by 0 days.

(21) Appl. No.: 14/884,893

(22) Filed: Oct. 16, 2015

(65) Prior Publication Data
US 2017/0108532 A1    Apr. 20, 2017

(51) Int. Cl.
*A61B 18/20* (2006.01)
*G01N 21/35* (2014.01)

(52) U.S. Cl.
CPC ............. *G01N 21/35* (2013.01); *A61B 18/20* (2013.01)

(58) Field of Classification Search
CPC .................. A61B 18/20; A61B 2018/2085
See application file for complete search history.

(56) References Cited

U.S. PATENT DOCUMENTS

| 8,630,322 | B2 * | 1/2014 | Dantus | H01S 3/0057 372/24 |
|---|---|---|---|---|
| 2005/0036667 | A1 * | 2/2005 | So | G06K 9/00127 382/128 |
| 2008/0308730 | A1 * | 12/2008 | Vizi | G02B 21/0048 250/309 |
| 2013/0149734 | A1 * | 6/2013 | Ammar | G01N 21/6408 435/29 |
| 2013/0211391 | A1 * | 8/2013 | Benyakar | A61B 18/20 606/10 |
| 2013/0301002 | A1 * | 11/2013 | Gruppetta | A61B 3/12 351/206 |
| 2015/0015879 | A1 * | 1/2015 | Papadopoulos | G02B 23/26 356/301 |

* cited by examiner

*Primary Examiner* — Jason McCormack
*Assistant Examiner* — Sean Luck
(74) *Attorney, Agent, or Firm* — Juan Carlos A. Marquez; Marquez IP Law Office, PLLC (57) ABSTRACT

An image processing method of two-photon structured illumination point scanning microscopy is disclosed. The image processing method includes the following steps: providing a laser light source; performing scanning and recording; and performing image reconstruction. The laser light source, which has photon energy that is half of the energy needed to let a molecule of a sample make a transition from ground state to a first excited state, is focused onto a focal plane of the sample. Then, the laser light source is accompanied with an image recording system to perform a plurality of segmented scanning and image recordings on the sample to generate a plurality of structured illumination images. Those structured illumination images are reconstructed to generate microscopic image of the sample. With the implementation of the present invention, the interference from image signal on the non-focal plane can be effectively reduced, thereby enhancing the resolution of microscopic image.

5 Claims, 12 Drawing Sheets

FIG. 4A $(x_{11}+\frac{1}{2}d), \varnothing = 0°$ $(x_{11}+\frac{7}{2}d), \varnothing = 360°$ $(x_{11}+\frac{13}{2}d), \varnothing = 720°$ $(x_{11}+\frac{19}{2}d), \varnothing = 1080°$

FIG. 4B

FIG. 4C $(x_{11}+\frac{3}{2}d), \varnothing = 120°$
$(x_{11}+\frac{9}{2}d), \varnothing = 480°$
$(x_{11}+\frac{15}{2}d), \varnothing = 840°$
$(x_{11}+\frac{21}{2}d), \varnothing = 1200°$

IMAGE PROCESSING METHOD OF TWO-PHOTON STRUCTURED ILLUMINATION POINT SCANNING MICROSCOPY

BACKGROUND OF THE INVENTION

1. Technical Field

This present invention relates to an image processing method of two-photon structured illumination point scanning microscopy, more particularly, to an image processing method of two-photon structured illumination point scanning microscopy that can be used in the observation of biological cell sample.

2. Description of Related Art

In our living environment, it is usually filled with all kinds of bacteria, viruses, or other factors that might endanger human health or environment. Therefore, biomedical research is always an important target in the scientific development process. In the research process, microscopic image technology plays an important role. Among them, microscopic image technology based on laser as a light source has further enhanced its resolution; therefore, it has provided a powerful tool for biomedical research field.

However, the prior art technology using laser as the light source for microscopic image is the so-called "single-photon microscopy", which adopts laser light with each photon energy sufficient to let the molecule in the sample-under-test make a transition to excited state.

Figure 1:
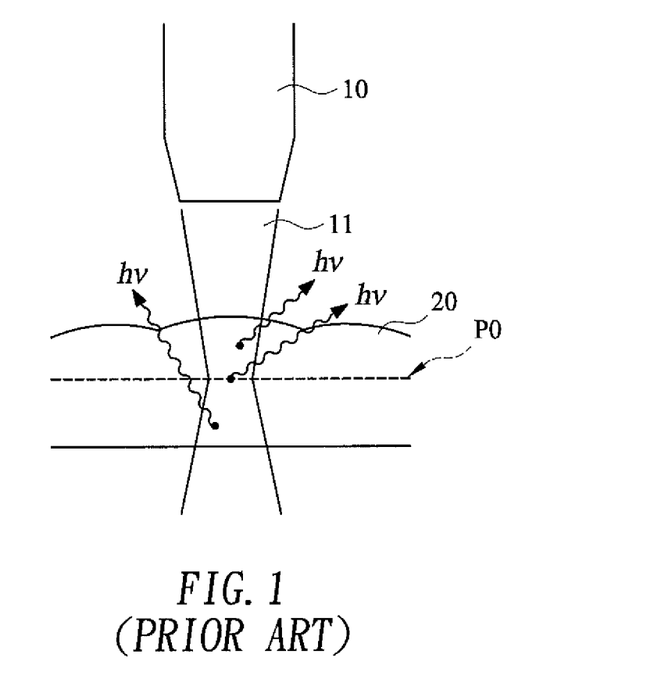
FIG. 1 is an illustration of the situation of the release of photon of molecule of sample-under-test when excited by laser light in the single-photon microscopy of the prior art.

As shown in FIG. 1, since the energy of each photon in the optical beam 11 of a laser light source 10 used in single-photon microscopy is sufficient to let a molecule in a sample-under-test 20 get excited, then make a transition back to a ground state from an excited state and release photon hv and get observed or recorded. Therefore, within the illumination path of the optical beam 11 emitted by the laser light source 10, all the molecules will have chance to get excited, then make a transition back to the ground state and release photon hv and get observed and recorded. A great part of the observed or recorded image signal is not generated by molecules on the focal plane P0 that the observer is originally planning to observe. Thus, the resolution of the microscopic image in the axial direction is reduced.

In order to solve the bad axial resolution issue of single-photon microscopy, "Two-Photon Scanning Microscopy (TPSM)" is thus proposed. The largest difference between two-photon microscopy and single-photon microscopy is: In two-photon scanning microscopy, the energy of each photon in the laser light source used is only half of the energy needed for the sample's molecule to make a transition from the ground state to the excited state. Under such condition, to excite the molecule in the sample to make a transition to the excited state, it is necessary to let the same molecule, at the same time, receive two incident photons and absorb them. That is, it is necessary to have two photons, at the same time, incident on the same spatial location. Therefore, only the molecules of the sample located at the focal spot of the laser light source will have higher probability to satisfy simultaneously temporal and spatial location limit and get excited. Consequently, the resolution of the obtained microscopic image in the axial direction will be greatly enhanced. However, due to the physical characteristic limit of optical component used to focus laser light source, especially the diffraction limit of the optical component, it will lead to the difficulty of the laser light source to be focused on smaller area. Therefore, even if two-photon scanning microscopy is adopted, the improvement on the resolution of the microscopic image is still limited.

Hence, how to improve or solve effectively the above problems so as to obtain microscopic image of higher resolution has become important target for related researchers or suppliers.

BRIEF SUMMARY OF THE INVENTION

The present invention is to solve the problems of lower resolution when observing smaller sample in the prior art microscopic image technology, especially the insufficient axial resolution problems along the optical axis direction.

The present invention provides an image processing method of two-photon structured illumination point scanning microscopy, comprising the following steps: providing a laser light source, wherein the laser light source is focused onto a focal plane of a selected focal length, which is included in a detection target area of a sample-under-test, and the laser light source is a Near Infrared Pulsed Laser, meanwhile, the photon energy of the laser light source is half of the energy needed to let a molecule of the sample-under-test make a transition from ground state to a first excited state; performing scanning and recording, which is to use the laser light source, accompanied with an image recording system, to make a plurality of segmented scanning and image recording along two different directions respectively on the focal plane within the detection target area, so as to generate a plurality of structured illumination images of the detection target area; and performing image reconstruction, which is to perform reconstruction operation on the structured illumination images so as to generate microscopic image of the detection target area, including the sample-under-test.

At least the following improvements can be achieved with implementation of the present invention:

1. Signal interference coming from out-of-focal-plane can be effectively reduced; and
2. The resolution of the microscopic image can be improved.

The detailed features and advantages of the present invention will be described in detail with reference to the preferred embodiment so as to enable persons skilled in the art to gain insight into the technical disclosure of the present invention, implement the present invention accordingly, and readily understand the objectives and advantages of the present invention by perusal of the contents disclosed in the specification, the claims, and the accompanying drawings.

DETAILED DESCRIPTION OF THE INVENTION

Figure 2:
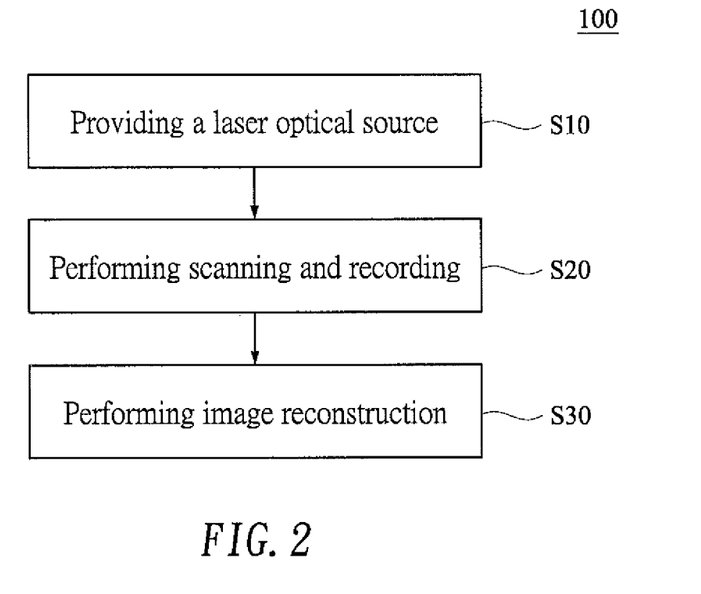
FIG. 2 is the flow chart of an embodiment of the present invention.

As shown in FIG. 2, an embodiment of the present invention provides an image processing method of two-photon structured illumination point scanning microscopy 100, comprising the following steps: providing of a laser light source (step S10); performing scanning and recording (step S20); and performing image reconstruction (step S30).

Figure 3:
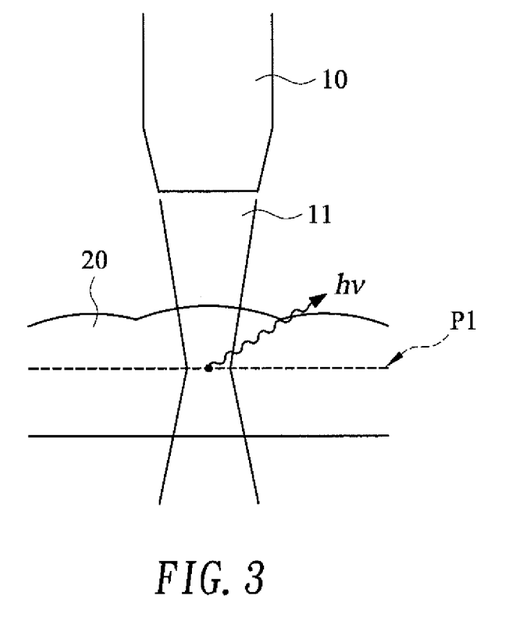
FIG. 3 is an illustration of the situation of the release of photon of molecule of sample-under-test when excited by laser light in an embodiment of the present invention.

As shown in FIG. 3, the step S10 of providing a laser light source is to focus a laser light source 10 onto a pre-selected focal plane P1 of sample-under-test 20, that is, it includes a focal plane P1 of pre-selected focal length of a detection target area A of the sample-under-test 20 that the observer is about to observe.

Figure 4A:
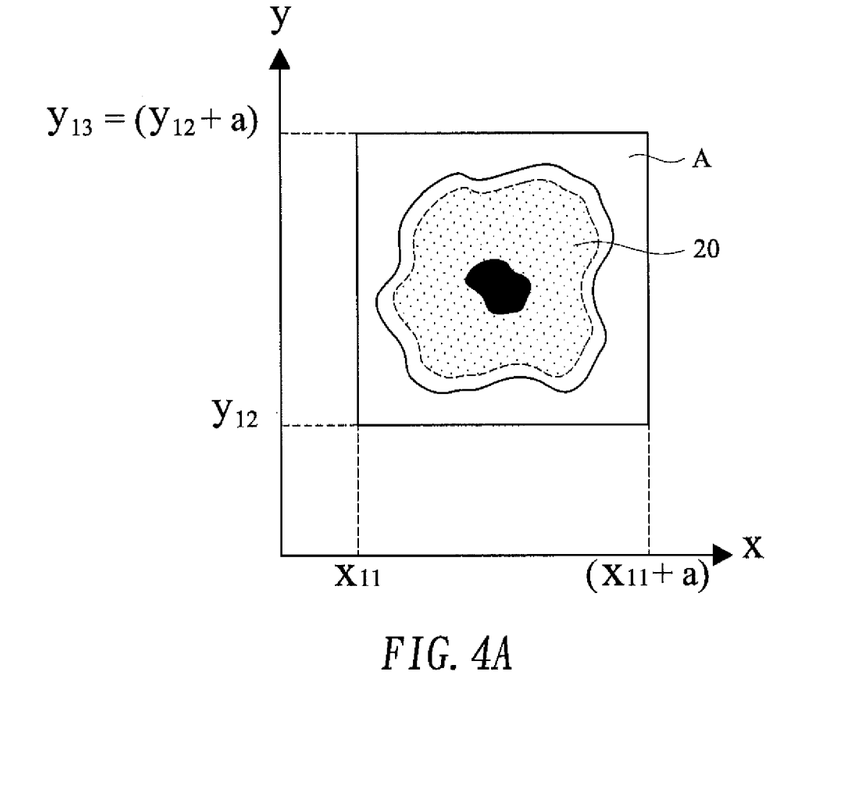
FIG. 4A is an illustration of a detection target area and a sample-under-test of an embodiment of the present invention.
Figure 4B:
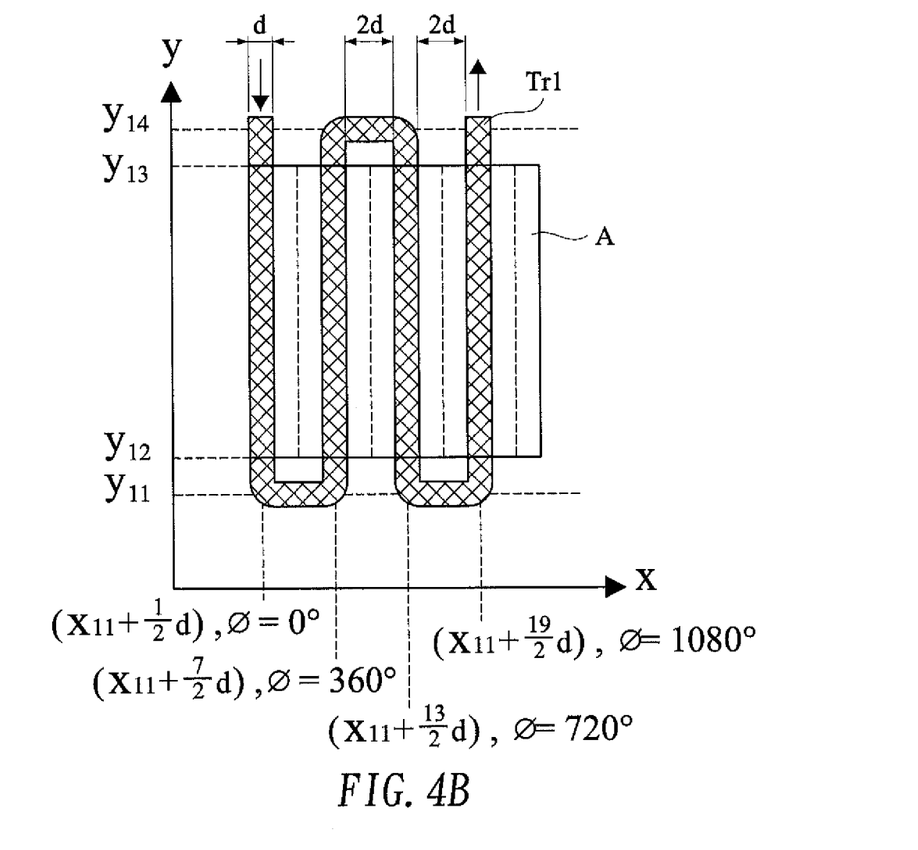
FIG. 4B is an illustration of the relative relation between a first scanning path and the detection target area and the sample-under-test for an embodiment of the present invention.

Please refer simultaneously to FIG. 4A and FIG. 4B, suppose the sample-under-test 20 is a cell sample, and the sample-under-test 20 is located at a pre-selected focal plane P1 of a square detection target area A. It is further supposed that the detection target area A is located between $x=x_{11}$ and $x=(x_{11}+a)$, and $y=y_{12}$ and $y=y_{13}=(y_{12}+a)$. That is, the detection target area A is a square area of both length and width of a.

During the step S10, the laser light source 10 with an optical beam 11 of a diameter d on the focal plane P1 is focused onto a location of coordinate $(x_{11}+d/2, y_{14})$ at the outside of the detection target area A on the selected focal plane P1.

The laser light source 10 used in this embodiment is light source of near infrared pulsed laser, meanwhile, the frequency or wavelength of the near infrared pulsed laser light source 10 is pre-selected so that the energy of each photon of optical beam 11 emitted by the near infrared pulsed laser light source 10 is half of the energy needed to let a molecule in the sample-under-test 20 make a transition from the ground date to a first excited state.

Since the energy of each photon emitted by the laser light source 10 of the embodiment is only half of the energy needed to let the molecule in the sample-under-test 20 make a transition from the ground state to the first excited state, hence, to excite the molecule in the sample-under-test 20 to make a transition to the excited state, it is necessary to let the same molecule receive, at the same time, two incident photons and absorb them.

That is, it is needed to have two photons, at the same time, incident on the same spatial location. Consequently, only the molecules of the sample-under-test 20 located at the focal spot of the laser light source 10 will have higher probability to satisfy simultaneously the temporal and spatial location limits and get excited, then release photon of hv when they get back to the ground state. Therefore, the axial resolution of the obtained microscopic image can be greatly enhanced. This is the so-called "Two-Photon Microscopy", or "Two-Photon Excitation Microscopy".

In addition, the near infrared pulsed laser light source 10 used in the embodiment can be light source of near infrared femtosecond pulsed laser of higher frequency.

This is because when the pulse frequency of the laser light source 10 is higher, that is, the period is shorter and then relatively its pulse width will be narrower. Therefore, the actual illumination time of the laser light source 10 in each period will be shorter, and the energy emitted by the laser light source 10 will be centered within shorter illumination time. Consequently, first, the energy utilization rate can be effectively enhanced; second, since the temporal limit range to be satisfied becomes smaller, the resolution of the image obtained can be further enhanced.

In the step S20 of scanning and recording, the laser light source 10 is used to do a plurality of segmented scanning respectively, along two different directions, on the detection target area A and the sample-under-test 20 within it. Generally speaking, it is to perform a plurality of segmented scanning along x axis direction and along y axis direction. Meanwhile, while the laser light source 10 is performing scanning on the detection target area A and the sample-under-test 20 within it, accompanied with the use of an image recording system, images are recorded so as to generate a plurality of structured illumination images 30.

The reason to use two-photon excitation microscopy in association with "Structured Illumination Microscopy" is because any hardware equipment usually has its physical limitation, which is especially true for optical component.

The work of image recording of the image recording system is done through camera formed by lens to focus optical beam from the sample onto photo-sensitive material or photo sensor. These optical beams from the sample will, after passing through the lens, due to the physical limit of the lens, lead to the reduction of the resolution of the image sensed by the photo-sensitive material or photo sensor.

In structured illumination microscopy, illumination light source of known structure of radiation pattern is projected onto the sample-under-test 20, then by summarizing the results obtained from different illumination methods and the structure of radiation pattern data of the illumination light source, the image of the sample-under-test 20 can then be inversely calculated by a computer. However, during the calculation process, the influences from all kinds of physical limiting factors of the hardware equipment can be considered and compensated or corrected, hence, the high resolution that cannot be obtained before can be obtained at this moment.

Through the above mentioned method, the structured illumination microscopy can break through the physical limit of hardware equipment such as the optical system. Therefore, this embodiment has associated simultaneously the use of two-photon excitation microscopy and the structured illumination microscopy so as to break through the physical limits of image recording system, and the resolution of the image obtained can be further enhanced.

First of all, in the structured illumination microscopy, the structure of radiation pattern of the light source must be known. Meanwhile, in order to facilitate the subsequent inverse estimation in the computer and to obtain highly accurate estimation result, the adopted structure of radiation pattern better be of simple geometric shape. For example, the illuminated area can be formed in a fringe shape of equal interval, or can be formed in regular and repeated geometric shape such as a grid shape. In the following, an example with the illuminated area formed in the fringe shape of equal interval will be taken for explanation.

As shown in FIG. 4B, while starting the step S20 of performing scanning and recording, first, let the illumination location of the laser light source 10 start from $(x_{11}+d/2, y_{14})$ and move along the first scanning path Tr1.

First scanning path Tr1 is mainly formed by a series of straight line segments parallel to y axis direction. Each straight line segment parallel to y axis will usually have an interval of 2d to the next neighboring line segment. Meanwhile, when the illumination location of the laser light source 10 moves from any line segment parallel to y axis to the next neighboring parallel line segment, its passing path will usually be a line segment parallel to x axis, or said a line segment that makes the illumination scope of the laser light source 10 totally located out of detection target area A.

Figure 4C:
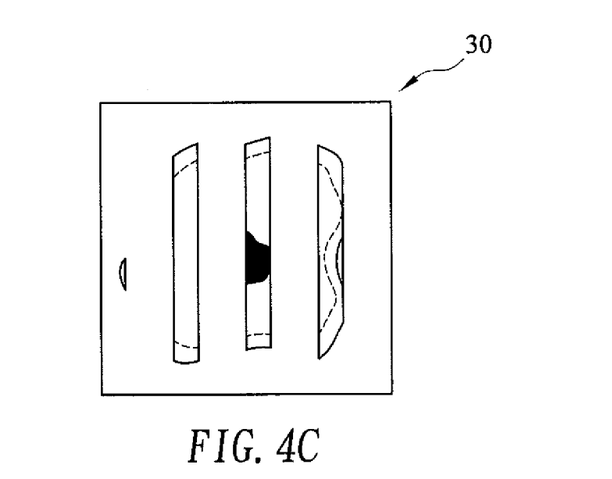
FIG. 4C is structured illumination image obtained from scanning illumination by laser light source along the first scanning path for an embodiment of the present invention.

Since the overlapped part between the first scanning path Tr1 and the detection target area A is a series of line segments parallel to but not connected to each other, hence, information sensed and recorded by the image recording system is a structured illumination image 30 of the fringe shape or a stripe shape as shown in FIG. 4C.

Figure 4D:
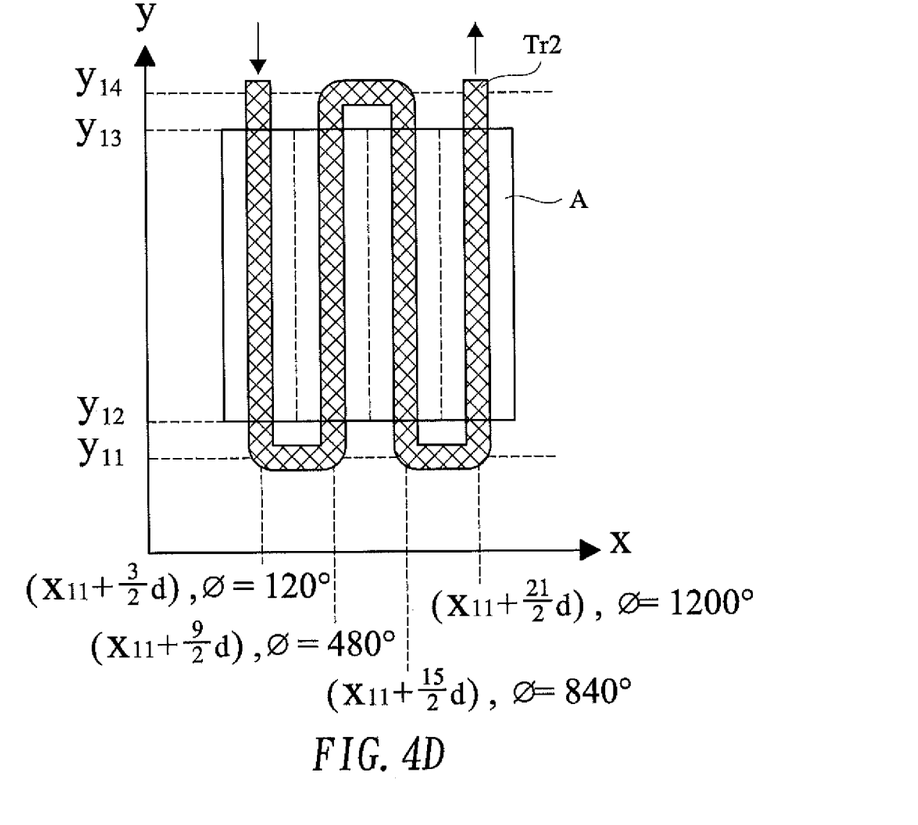
FIG. 4D is an illustration of relative relation between a second scanning path and the detection target area and the sample-under-test for an embodiment of the present invention.
Figure 4E:
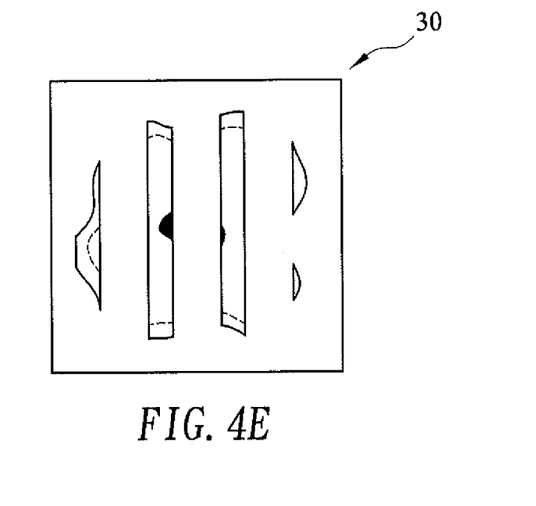
FIG. 4E is structured illumination image obtained from scanning illumination by a laser light source along the second scanning path for an embodiment of the present invention.
Figure 4F:
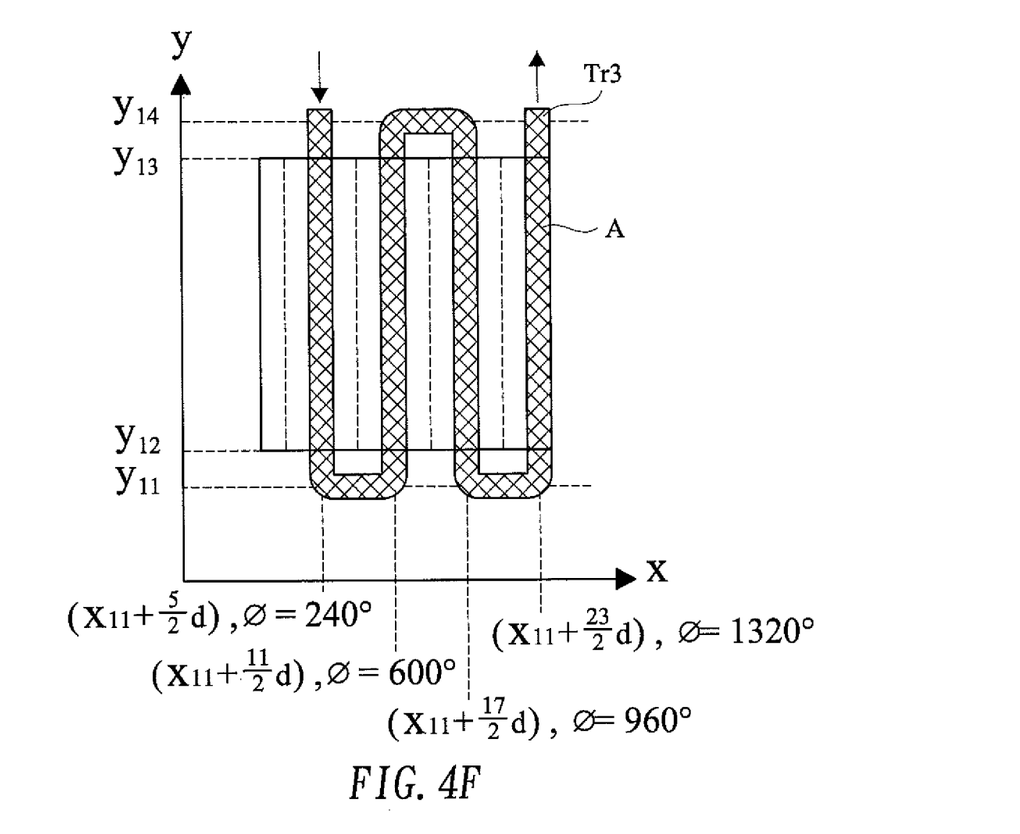
FIG. 4F is an illustration of relative relation between the third scanning path and the detection target area and the sample-under-test for an embodiment of the present invention.
Figure 4G:
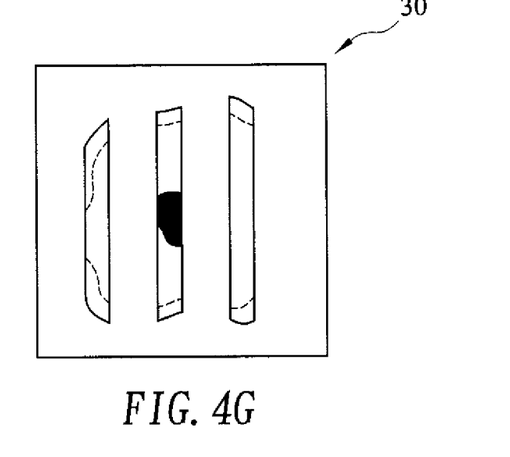
FIG. 4G is structured illumination image obtained from scanning illumination by a laser light source along the third scanning path for an embodiment of the present invention.

As shown in FIG. 4D to FIG. 4G, next, let the illumination location of the laser light source 10 move in sequence and respectively along a second scanning path Tr2 and a third scanning path Tr1. Therefore, the image recording system can then sense and record, as shown in FIG. 4E and FIG. 4G, two additional structured illumination images 30, of the fringe shape or the stripe shape and of equal interval, which record respectively different parts of detection target area A.

Figure 4H:
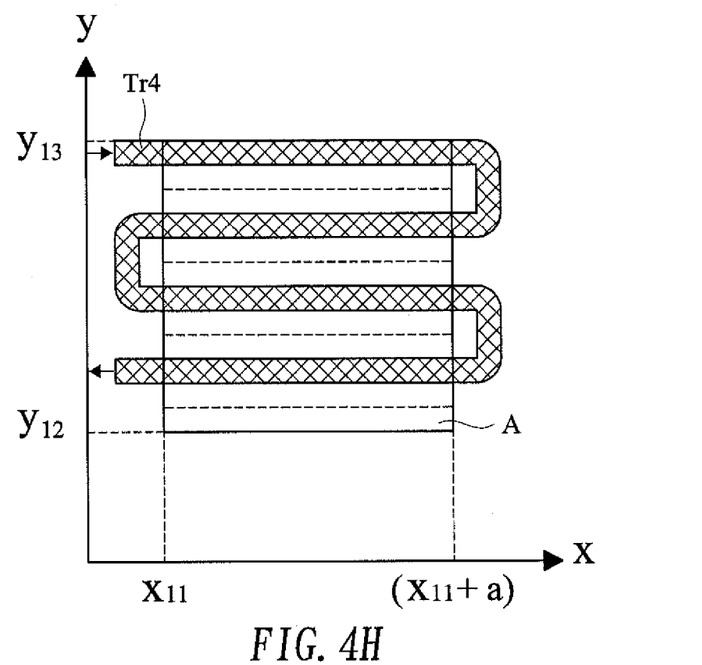
FIG. 4H is an illustration of relative relation between a fourth scanning path and the detection target area and the sample-under-test for an embodiment of the present invention.
Figure 4I:
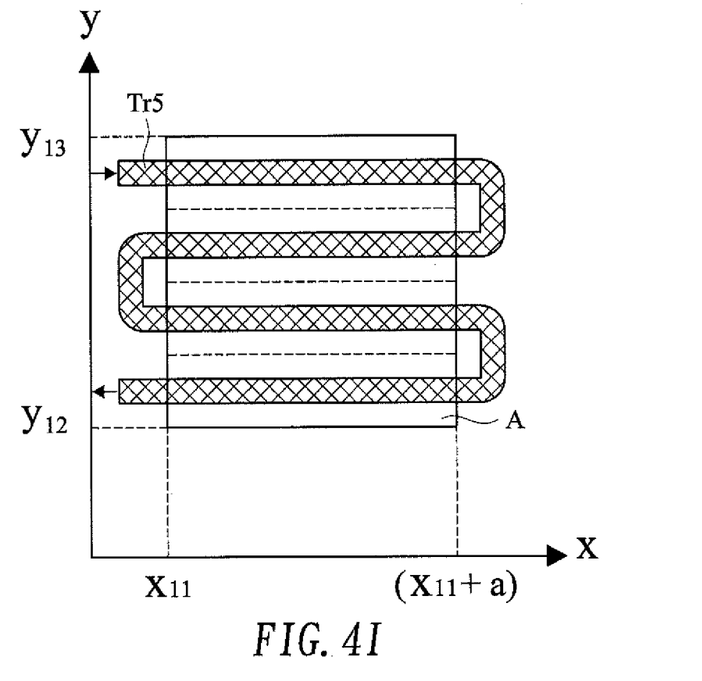
FIG. 4I is an illustration of relative relation between a fifth scanning path and the detection target area and the sample-under-test for an embodiment of the present invention.
Figure 4J:
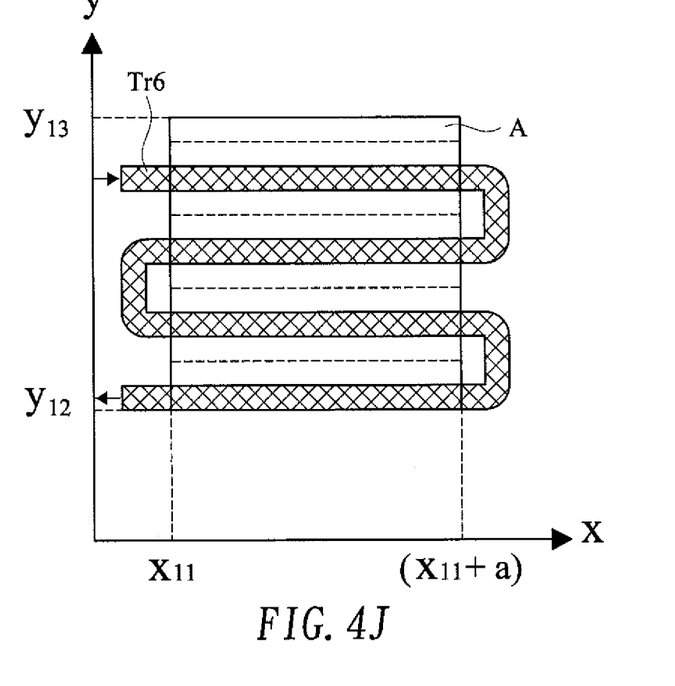
FIG. 4J is an illustration of relative relation between a sixth scanning path and the detection target area and the sample-under-test for an embodiment of the present invention.

Further shown in FIG. 4H to FIG. 4J, next, the same method is taken, let the illumination locations of the laser light source 10 move and scan respectively along a fourth scanning path Tr4, a fifth scanning path Tr5 and a sixth scanning path Tr6, therefore, three structured illumination images 30 with outlines of a series of parallel the fringe shapes or the stripe shapes of equal interval are obtained.

From the above description, it can be seen that: in the present embodiment, the detection target area A is divided into three blocks respectively along x axis direction and along y axis direction.

When the illumination locations of the laser light source 10 move along the first scanning path Tr1, the second scanning path Tr2 and the third scanning path Tr3, it means that each set of blocks divided, along x axis in the detection target area A are illuminated respectively, and then three corresponding structured illumination images 30 are obtained. The images of all locations in the detection target area A are recorded within these three structured illumination images 30.

When the illumination locations of the laser light source 10 move along the fourth scanning path Tr4, the fifth scanning path Tr5 and the sixth scanning path Tr6, it means that each set of blocks divided along y axis in the detection target area A are illuminated respectively, and then three additional corresponding structured illumination images 30 are obtained. The images of all locations in the detection target area A are recorded within these three structured illumination images 30.

The step S30 of performing image reconstruction is to input six structured illumination images 30 obtained from the previous step into the computer, and then a series of reconstruction operations are carried out. Thus, microscopic images of higher resolution of the sample-under-test 20 are calculated and generated.

Figure 4K:
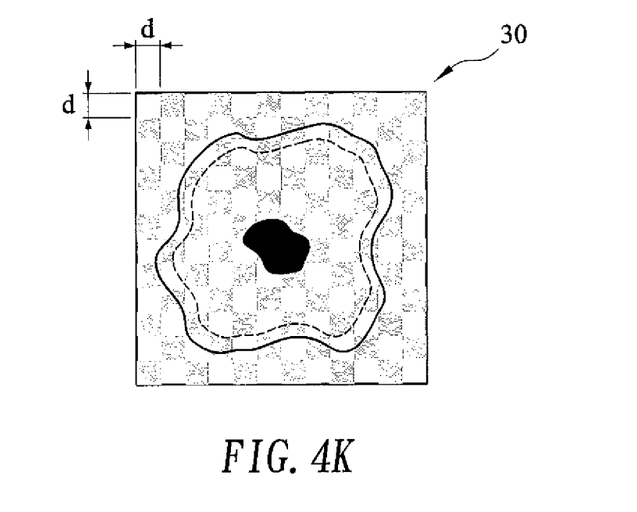
FIG. 4K is an illustration of the scanning illumination area of laser light source in grid shape for an embodiment of the present invention.

Although the above example is explained when the illuminated area is displayed in fringe shape of equal interval, yet as mentioned above, the scanning illumination area of the laser light source 10 of the embodiment of the present invention can also be of the grid shape as shown in FIG. 4K. Meanwhile, its operation is almost the same as that of the illuminated area of the fringe shape of equal interval, therefore, it will not be repeatedly stated here.

Figure 5:
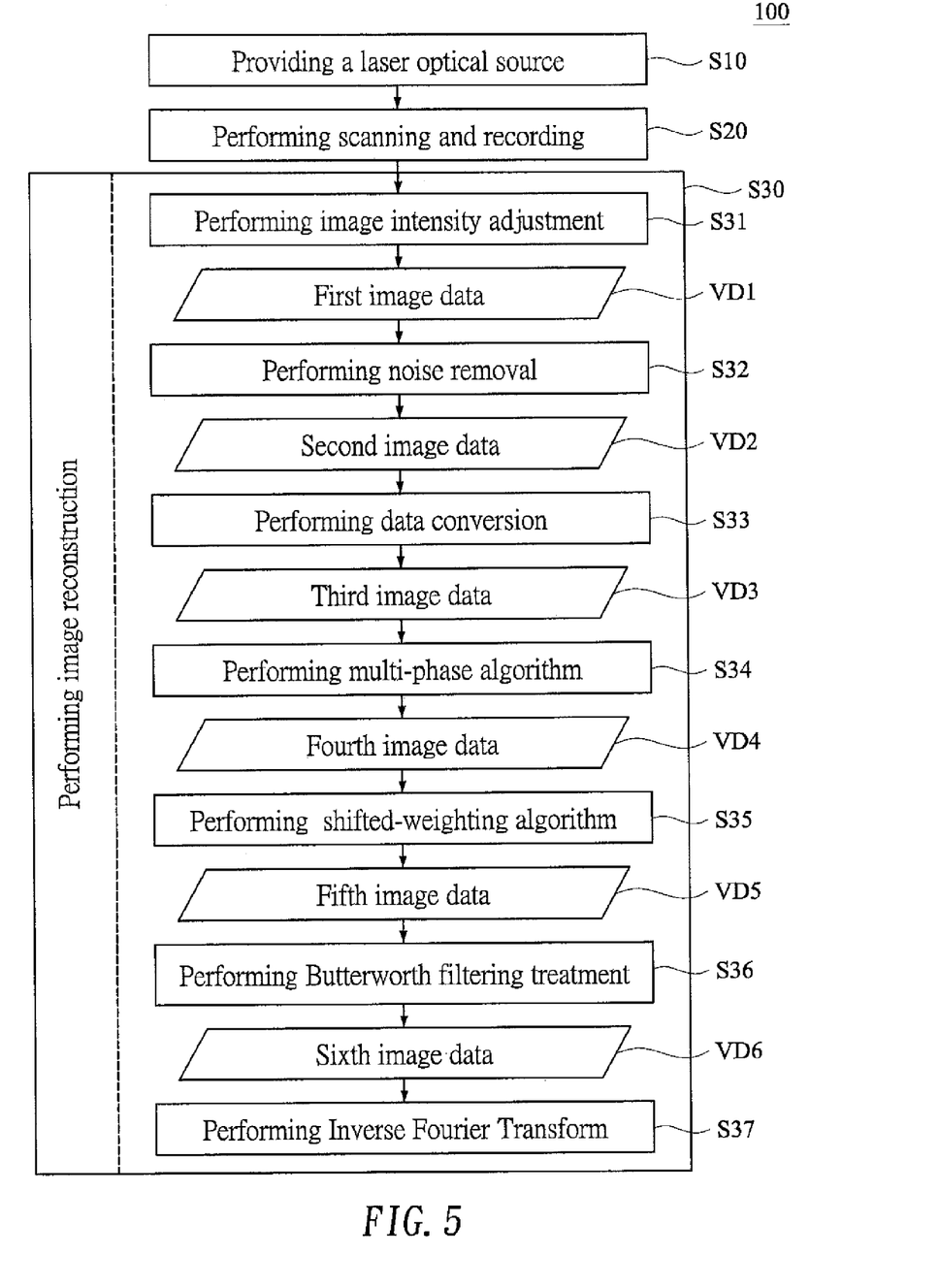
FIG. 5 is another step flow chart for an embodiment of the present invention.

As shown in FIG. 5, the step S30 comprises the following sub-steps: performing image intensity adjustment (step S31); performing noise removal (step S32); performing data conversion (step S33); performing Multi-Phase Step Algorithm (step S34); performing shifted-weighting algorithm (step S35); performing Butterworth filtering treatment (step S36); and performing inverse Fourier transform (step S37).

The reason to conduct the step S31 of performing image intensity adjustment is because when the image recording system is sensing an image, maybe due to reasons such as mechanical structure error or signal disturbance in the sensing circuit, the sensed and recorded image signal intensity of each location in the detection target area A might be a little bit different. Therefore, the intensity of each structured illumination image obtained from the previous step should be adjusted to be consistent to generate the first image data VD1 to be used by the subsequent step.

The step S32 of perform noise removal is to remove the background noise, generated by the image recording system, within the first image data VD1. First, the background noise of the image recording system is found out, and generally this is the so-called white noise, then the background noise in the image recording system is used as a base model, for removing the noise, to remove the noise in the first image data VD1. Then a second image data VD2 that can be used and processed in the next step is generated.

The step S33 of performing data conversion is to perform Fourier transform on the second image data VD2 generated in the previous sub-step after filtering out the noise, that is, the original electronic signal data is performed with variable conversion to frequency domain so as to generate a third image data VD3 to be used in the subsequent processing step.

The step S34 of Performing Multi-Phase Step Algorithm is to process the third image data VD3 using operations such as linear simultaneous solution and phase estimation. Please refer again to FIG. 4B, FIG. 4D and FIG. 4F, take this embodiment as example, since in the previous step S20, the illumination location of the laser light source moves along three different scanning paths Tr1~Tr3 to illuminate the detection target area A. Meanwhile, after scanning is made along each scanning path and after illumination is made on the detection target area A, it will form a series of fringe shape or stripe shape illumination blocks of equal interval.

Suppose the illumination intensity of a first stripe illumination block (located at the straight line of $x=(x_{11}+d/2)$) formed by the laser light source 10 when it is scanning and illuminating in the detection target area A along the first scanning path Tr1 has a phase angle of 0° relative to the spatial location in the x axis direction, then the illumination intensities of the rest stripe shape illumination blocks will have phase angles, relative to the spatial locations in the x axis direction, in the order of 360°, 720° and 1080°. This is because, from the view point of the phase angles, the phase difference between two neighboring stripe shape illumination blocks is just a complete period, that is, a difference of 360°.

Similarly, the phase angle of each stripe shape illumination block formed by the laser light source 10 in the detection target area A when it is scanning along the second scanning path Tr2 will be respectively 120°, 480°, 840° and 1200°; and the phase angle of each stripe shape illumination block formed by a scanning along the third scanning path Tr3 will be respectively 240°, 600°, 960° and 1320°.

That is, when the laser light source 10, in the detection target area A, is scanning and illuminating along three different scanning paths, and the detection target area A is evenly divided into three sets of blocks, then the signal intensities of three structured illumination images 30 obtained respectively will form three sets of different phase angle distributions along the spatial locations in x direction, and the phase difference between the signal intensities of any two structured illumination images 30 is just 120°.

Similarly, after the illumination location of the laser light source 10 scans and illuminates along the fourth scanning path Tr4, the fifth scanning path Tr5 and the sixth scanning path Tr6, three structured illumination images 30 in another direction can be obtained again. The differences of phase distributions of the signal intensities of these three structured illumination images 30, relative to the spatial locations in y direction, are just 120°.

Since the previously obtained six structured illumination images 30 record respectively image data of three different phases in x direction and y direction, hence, when the step S34 of performing Multi-Phase Step Algorithm is conducted, the number of phase to be processed will be three. Its processing method is to use operations such as linear simultaneous solution and phase estimation to perform three-phase operation on the third image data VD3 so as to estimate the actual image data of the detection target area A and to generate a fourth image data VD4.

The step S35 of performing shifted-weighting algorithm is then conducted. The main factor causing a blurred image or bad resolution in the final obtained image data is the so-called emission point spread function. The emission point spread function, after the Fourier transform as in the previously step S33 mentioned, will become optical transfer function (OTF).

Therefore, in order to improve the resolution of the final obtained image, it is necessary to use at least one filter, meanwhile, angular spectrum calculation should be used to filter out the optical transfer function in the fourth image data VD4. Moreover, the filters used in the present embodiment are mainly Wiener filter or optical transform function filter.

In addition, the location, in the frequency domain space, of the spectral data after processing through the above mentioned step S34 is generally incorrect. Therefore, calculation is needed to shift the fourth image data VD4 to correct location in the frequency domain space, after that, the spectral data shifted to the correct location are combined. After a treatment of the above mentioned method, a fifth image data VD5 can then be obtained.

The step S36 of performing Butterworth filtering treatment is to perform filtering treatment on the fifth image data VD5 generated from the previous sub-step through a Butterworth filter so as to generate a sixth image data VD6. This is because, during the image reconstruction process, some vertical stripes and horizontal stripes will be formed in the image data. These stripes, in the spectrum, are the so-called "residual points". Moreover, the main purpose to perform Butterworth filtering treatment is to filter out these residual points, that is, to remove the stripe phenomenon generated in the reconstructed image.

The step of performing inverse Fourier transform is to perform inverse Fourier transform on the sixth image data VD6 that is previously treated with Fourier Transform as well as a series of operations and filtering treatment so as to convert the image again into actual image data, then a low noise and high resolution microscopic image in the detection target area A can be obtained, especially the microscopic image in the sample-under-test 20.

Figure 6:
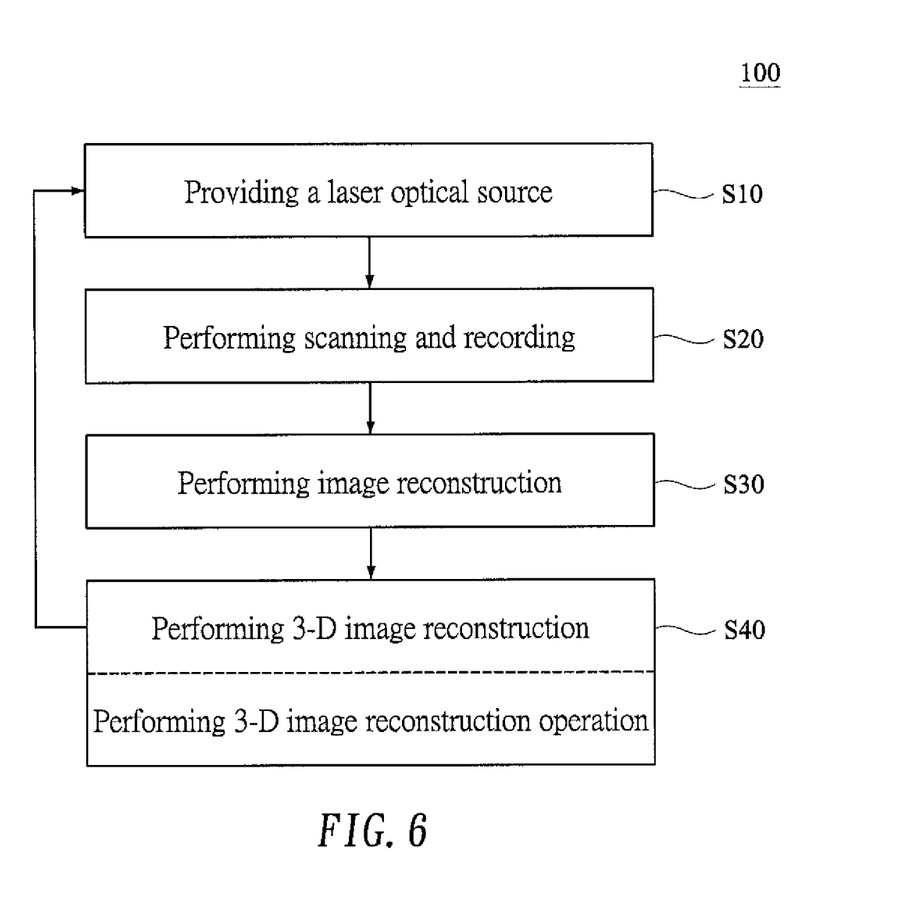
FIG. 6 is the flow chart of further adding of the step of performing a 3-D image reconstruction for an embodiment of the present invention.
Figure 7:
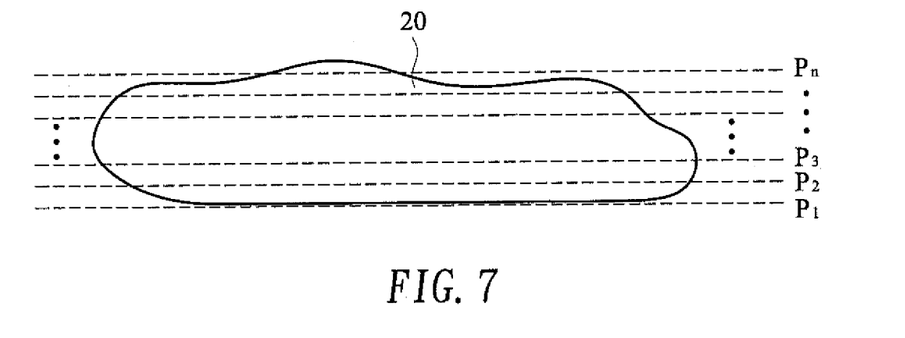
FIG. 7 is an illustration of the distribution method of focal plane in the 3-D image reconstruction step for an embodiment of the present invention.

As shown in FIG. 6 and FIG. 7, after the step S30 of performing image reconstruction, a 3-D image reconstruction step can be further added.

The 3-D image reconstruction step is to repeatedly conduct steps of providing a laser light source (step S10), performing scanning and recording (step S20) and performing image reconstruction (step S30), meanwhile, at each repeated conduction of these steps, the laser light source 10 is sequentially focused onto the focal plane P1, P2, P3, . . . , Pn of different focal length on the detection target area A. Through the conduction of step S20 and step S30, a plurality of microscopic images on these focal planes P1, P2, P3, . . . , Pn within the detection target area A are obtained. Later on, a 3-D image reconstruction operation is conducted on these microscopic images. After 3-D image reconstruction operation, a 3-D image sample-under-test 20 of high resolution can be obtained.

From the above explanation, it can be seen that: the image processing method 100 of two-photon structured illumination point scanning microscopy provided in this embodiment can indeed reduce effectively the interference of signal coming from the external side of the focal plane, in the meantime, the resolution of the microscopic image can be enhanced as well.

The features of the present invention are disclosed above by the preferred embodiment to allow persons skilled in the art to gain insight into the contents of the present invention and implement the present invention accordingly. The preferred embodiment of the present invention should not be interpreted as restrictive of the scope of the present invention. Hence, all equivalent modifications or amendments made to the aforesaid embodiment should fall within the scope of the appended claims.

What is claimed is:

1. An image processing method of two-photon structured illumination point scanning microscopy, comprising the following steps:

providing a laser light source, wherein the laser light source is focused onto a focal plane of a selected focal length, which is included in a detection target area of a sample-under-test, and the laser light source is a Near Infrared Pulsed Laser, meanwhile, the photon energy of the laser light source is half of the energy needed to let a molecule of the sample-under-test make a transition from ground state to a first excited state;

performing scanning and recording, which is to use the laser light source, accompanied with an image recording system, to make a plurality of segmented scanning and image recording along two different directions respectively on the focal plane within the detection target area, so as to generate a plurality of structured illumination images of the detection target area; and performing image reconstruction, which is to perform reconstruction operation on the structured illumination images so as to generate microscopic image of the detection target area, including the sample-under-test; wherein the step of performing image reconstruction comprises the following sub-steps;

performing image intensity adjustment, wherein intensities of the structured illumination images are adjusted to be consistent so as to generate a first image data;

performing noise removal, wherein background noise of the image recording system is used as a base model for removing noise so as to remove the noise in the first image data and then to generate a second image data;

performing data conversion, wherein the second image data is Fourier transformed to generate a third image data;

performing a Multi-Phase Step Algorithm, wherein the third image data is processed with a linear simultaneous solution and phase estimation to generate a fourth image data;

performing a shifted-weighting algorithm, wherein the fourth image data is calculated with an angular spectrum and filtered by at least one filter to filter out an optical transform function, wherein a shift in the fourth image data is modified to generate a fifth image data;

performing Butterworth filtering treatment, wherein the fifth image data is passed through a Butterworth filter to generate a sixth image data; and performing an inverse Fourier transform on the sixth image data to obtain an image of the detection target area, including the sample-under-test.

2. The image processing method of claim 1, wherein the near infrared pulsed laser light source is a near infrared femtosecond pulsed laser light source.

3. The image processing method of claim 1, wherein illuminated areas in the structured illumination images show a fringe shape of equal interval.

4. The image processing method of claim 1, wherein illuminated areas in the structured illumination images show a gird chessboard shape.

5. The image processing method of claim 1, wherein after the step of performing image reconstruction, a 3-D image reconstruction step can be is further added, which is to conduct repeatedly the step of providing of a laser light source, the step of performing scanning and recording and the step of performing image reconstruction, meanwhile, during each repeated conduction of the step of providing of a laser light source, the laser light source is focused onto a focal plane of different focal length of the detection target area, moreover, through step of performing scanning and recording, and step of performing image reconstruction, a plurality of microscopic images of the detection target area on those focal planes are obtained, meanwhile, those microscopic images are then conducted with a 3-D image reconstruction operation so as to generate a 3-D image of the sample-under-test.

* * * * *